(12) United States Patent
Barrows (10) Patent No.: US 9,649,330 B2
(45) Date of Patent: May 16, 2017

(54) HYDROGEL TATTOO PROTECTION AND AFTERCARE SYSTEM

(71) Applicant: Thomas Barrows, Dallas, TX (US)

(72) Inventor: Thomas Barrows, Dallas, TX (US)

( * ) Notice: Subject to any disclaimer, the term of this patent is extended or adjusted under 35 U.S.C. 154(b) by 0 days.

(21) Appl. No.: 14/155,453

(22) Filed: Jan. 15, 2014

(65) Prior Publication Data

US 2014/0200196 A1     Jul. 17, 2014

Related U.S. Application Data

(60) Provisional application No. 61/753,737, filed on Jan. 17, 2013.

(51) Int. Cl.
| | | |
|---|---|---|
| *A61K 31/734* | (2006.01) | |
| *A61L 26/00* | (2006.01) | |
| *C08L 5/04* | (2006.01) | |

(52) U.S. Cl.
CPC .......... *A61K 31/734* (2013.01); *A61L 26/008* (2013.01); *A61L 26/0023* (2013.01); *A61L 26/0061* (2013.01)

(58) Field of Classification Search
CPC . A61K 31/734; A61L 26/008; A61L 26/0023; A61L 26/0061; C08L 5/04
USPC .......................................................... 514/54
See application file for complete search history.

(56) References Cited

U.S. PATENT DOCUMENTS

| | | | |
|---|---|---|---|
| 4,689,301 A * | 8/1987 | Adet et al. ..................... 435/182 |
| 2002/0122771 A1 | 9/2002 | Holland | |
| 2003/0021832 A1* | 1/2003 | Scherr .......................... 424/445 |
| 2005/0276858 A1* | 12/2005 | Kao et al. ..................... 424/487 |
| 2006/0182788 A1 | 8/2006 | Singh | |
| 2008/0166385 A1* | 7/2008 | Durance et al. .............. 424/405 |
| 2010/0069927 A1 | 3/2010 | Clark | |
| 2010/0093917 A1* | 4/2010 | Torii ....................... C08F 20/06 524/539 |
| 2010/0291055 A1* | 11/2010 | Athanasiadis ...... A61L 26/0052 424/94.1 |
| 2011/0293699 A1 | 12/2011 | Bennett | |
| 2012/0009275 A1 | 1/2012 | Asfaw | |
| 2012/0298777 A1 | 11/2012 | Holladay | |

* cited by examiner

*Primary Examiner* — Blessing M Fubara (57) ABSTRACT

A wound care dressing that combines a sodium alginate hydrogel spread and a calcium solution spray to create a transparent membrane over damaged skin eliminating the need for a secondary dressing. The calcium dissolved in alcohol displaces sodium from the hydrogel spread, resulting in the formation of the membrane. The membrane decreases healing time by fostering hemostasis, a moist wound healing environment and absorption of exudate and blood from the wound. The membrane also provides an immediate cooling effect for the damaged skin. Once the wound is cleaned, the user applies the hydrogel and covers it with a mist of spray which creates a film layer. The membrane is transparent and flexible such that the skin surface is still visible and the membrane will not be dislodged as the skin is manipulated. The dried surface of the membrane is not tacky, eliminating the need for a secondary dressing.

6 Claims, 12 Drawing Sheets

HYDROGEL TATTOO PROTECTION AND AFTERCARE SYSTEM

CROSS-REFERENCE TO RELATED APPLICATIONS

This application is a non-provisional application that claims priority of U.S. Provisional Patent Application No. 61/753,737 filed Jan. 17, 2013, and entitled "Hydrogel Tattoo Protection and Aftercare System," the contents of which are hereby incorporated by reference.

TECHNICAL FIELD

This invention relates to wound care and more particularly to a system for tattoo wound care dressing.

DESCRIPTION OF PRIOR ART

Tattoos are a popular form of body art that has existed for centuries. Modern tattoos are applied using needles and ink. The tattoo process creates micro-punctures in the dermis into which ink is deposited for the purpose of creating a permanent tattoo. The micro-punctures of the tattoo wound secrete exudate immediately. The exudate commonly results from inflammation or injury and is released from tissues or blood vessels.

When the skin is tattooed, a tattoo needle is used to create countless micro-punctures into the dermis. The dermis, located below the epidermis, is the sensitive connective tissue layer of the skin which contains nerve endings, sweat, sebaceous glands, blood and lymph vessels. The tattoo needle deposits particles of pigment into the dermis to create a permanent tattoo. The ink deposited in the dermis may escape through the micro-punctures on the dermis. This loss of ink may potentially limit or decrease the technical quality and visual appeal of the tattoo. In addition, the ink seeping from the fresh tattoo may stain clothes or any other surface the ink contacts. Several hours after the tattoo has been created, continued bleeding and wound exudation may contribute to the loss of ink from the tattoo.

Exudate is any fluid that is secreted from the blood vessels and tissues through lesions or inflamed areas of the body. Exudate is a purulent or clear fluid that oozes from wounds on the body. Exudate fluid is generally composed of cells, platelets, proteins, serum, white blood cells, red blood cells, and similar body matter or fluids. The flow of exudate away from the wound may also reduce infection. However, as the exudate dries, a crust is formed that not only depletes the moist wound healing environment but also tears away the adherent exudate from the wound. The removal of the exudative crust commonly results in secondary injury to the wound as well as ink loss in the case of tattoo wounds. The best wound covers keep the wound moist while also absorbing exudates to expedite healing of the wound. A moist wound healing environment accelerates the recovery time and also reduces the amount of scarring on the wounded tissue.

Tattoo parlors have a variety of methods to address the wound created by a fresh tattoo. Existing wound care management of tattoo-created wounds usually consists of the application of petroleum-based products to create an occlusive layer over the wound as well as a secondary dressing, most often not of medical grade quality. Typical secondary dressings used for tattoos are plastic wrap for food or gauze. These commonly available household materials do not absorb wound exudate and may fail to control bleeding. These traditional wound dressing materials also fail to adequately prevent ink loss. The plastic wrap creates a seal around the skin, preventing oxygen from permeating the dressing and reaching the wound and thereby trapping blood and wound exudates against the surface of the wounded skin. Additionally, the body fluids and lost ink become trapped against the skin and are heated by body heat. This moist and warm environment is an ideal breeding ground for bacterial growth and infection. Another method of treating the wound is to use acrylate polymers dissolved in hexamethyldisiloxane or isooctane or "NuSkin". Although acrylate polymers, similar in function to superglue or Dermabond, do not require a secondary dressing, they are difficult to remove and may remain affixed to the wound for days or weeks. Unfortunately, acrylate polymers are also very painful to remove from the skin and wounded area making them undesirable for a tattoo wound.

For a tattoo wound, the formation of a scab or exudative crust is highly undesirable and detrimental to the freshly applied tattoo art. Scabs also form a barrier to the generation of new tissue. Skin regenerates much faster and the risk of infection from airborne pathogens is lower with a moist wound. The premature removal of a scab or exudative crust can cause injury to the healing wound as well as potential loss of tattoo pigment, which is highly undesirable after the pain and expense of obtaining the tattoo.

Recently, hydrogels have been used as a dressing for wound care. Hydrogels are comprised of materials that create intermolecular entanglements using water for dispersal. Hydrogels are highly absorbent natural or synthetic polymers, with high water content, that possess a degree of flexibility similar to natural tissue. Due to their high water volume, hydrogels can keep a wound moist yet still absorb exudate. While non-crosslinked hydrogels can be spread over a surface with irregular boundaries, the outer surface remains sticky, requiring a secondary dressing to prevent random debris from clinging to the wound covering. Also, traditional hydrogels are not optimal for a patient who is not immobilized. A mobile patient would quickly displace a traditional hydrogel dressing that was not secured by a secondary dressing since the sticky surface may adhere to outside objects and become displaced. Particles may become attached to the sticky surface or the hydrogel may inadvertently be dislodged from the wounded area if the patient rubs the hydrogel against a surface. Secondary dressings are necessary to prevent these issues and maintain the position of the traditional hydrogel dressing. Alternatively, hydrogels can be cross-linked by radiation, free radicals, or other means to result in a rubbery material that can be cut into various forms but a secondary dressing will still be required to secure the material to the wound and surrounding skin. These rubberized hydrogels are available in strips that may need trimming to accommodate an irregularly shaped wound. In the case of an especially large wound, an impractically high number of strips may be required.

The present system and method is a spreadable hydrogel matrix treated with a film forming mist to form a flexible membrane over a tattoo or wound. In this embodiment, the flexible membrane is understood to be transparent. The present system improves wound healing for a freshly applied tattoo as well as reduces the formation of exudative crusting and reduces ink loss. The present invention also absorbs exudate, adheres to the moist wound surface and can be removed with little or no pain at the wounded skin surface. It can be used on a wound of practically any size or shape due to its accommodating and adaptable nature. The present system and method also prevents loss of ink from the tattooed surface and allows the tattoo art to be immediately visible to the person and whoever wants to see the new tattoo.

SUMMARY OF THE INVENTION

The present system and method is a novel formulation for wound care dressings that combines a hydrogel spread and mineral spray solution to create a transparent membrane or film layer over the skin or tattooed surface. The spray reacts with the hydrogel to create a film layer, which may be tacky at the surface adjacent to the skin but non-tacky on the surface exposed to the environment, eliminating the need for a secondary dressing. In this embodiment, the hydrogel contains sodium alginate and the spray contains a calcium compound dissolved in a liquid such as alcohol and/or water to displace the sodium from the alginate resulting in film formation. The present system and method has many benefits over the prior art such as fostering hemostasis to a fresh tattoo, a moist wound healing environment, and ability to absorb any ongoing exudate from the micro-punctures created during the creation of the tattoo on the skin. The present wound care system plays a pivotal role in hemostasis, which controls and eventually stops the blood flow. Hemostasis involves constriction of the blood vessel, temporary blockage of the blood vessel and coagulation of blood until the damaged tissue is repaired. The hydrogel spread of the present wound care system blocks the damaged blood vessels and also keeps the coagulated blood and exudates contained within the film layer. The present wound care system also traps moisture around the wound to promote faster healing in the moist environment. The flexible cover formed by the combination of the hydrogel spread also absorbs the exudate that seeps from the wound as the wound heals. The present invention also has the benefit of providing an immediate evaporative cooling effect to the skin and is especially beneficial in treating burn wounds.

After the completion of a fresh tattoo on the skin of the user, the wounded area is gently cleansed of any extraneous matter such as ink, blood, or surface exudate. The user would then spread a thin layer of the hydrogel matrix over the entire wounded area, extending the hydrogel matrix slightly onto the adjacent, non-wounded skin. The user would then treat the hydrogel matrix spread over the wound with a fine mist of spray solution. As the spray covers the hydrogel matrix, a film cover is instantaneously created over the hydrogel matrix. The wound care system is functional within seconds of combining the hydrogel matrix and the spray solution. In addition, the surface of the film is smooth and not tacky as one would expect a gel coating to be. Since the surface is not sticky, no additional wound dressing is required as is commonly required with more traditional hydrogel wound dressings. Extraneous debris and contaminants will not adhere to the film as the film is not tacky on the exterior, exposed surface.

The hydrogel matrix is furthered strengthened by the presence of wound exudate since the additional moisture from the exudate keeps the hydrogel moist and strengthens the connection between the film and tattooed surface on the skin. As exudation from the wound diminishes, the hydrogel matrix dries and weakens. The drying hydrogel begins to loosen from the surface of the skin. The wound care system is promptly removed from the surface of the skin by gently rubbing the film surface, such as with a moist towel or wipe, until the wound care system detaches from the skin. Alternatively, the wound care system may be soaked in water, which will result in swelling as the hydrogel absorbs the water and will eventually release its bond to the skin.

The wound care system also includes a calcium compound dissolved in a liquid such as alcohol and/or water. In this embodiment, calcium chloride is preferred; however other salts of calcium may be used such as calcium lactate gluconate. Alternatively, solutions not containing calcium salts may be used as long as a divalent cation replaces the calcium. Divalent cations, i.e. ions possessing a double positive charge, crosslink two carboxylic acid groups of adjacent alginate molecules to form the film surface. Thus, magnesium, strontium, barium, zinc or other divalent cation may be used. It is critical that only deionized water be used in the composition of the hydrogel since hard water may contain calcium and magnesium that would interact and interfere with the chemistry of the present system and method.

Calcium alginate is useful in promoting hemostasis, or the cessation of the flow of blood, making calcium alginate an attractive material for the wound care system. The thickness of the resulting calcium alginate film layer is a function of the concentration of the alginate in the gel and the concentration of the applied calcium. The spray causes the alginate to coagulate and form a film layer after application of the hydrogel to the skin. The hydrogel matrix and the film surface exchange ions, which alters the solubility of the hydrogel components increasing the thickness of the hydrogel.

An ion exchange interaction between the hydrogel and spray at the film surface alters the solubility of the hydrogel components, which increases the thickness of the hydrogel, improves skin adhesion via the addition of tack agents, controls bleeding through the use of hemostatic agents, and provides a semi-permeable moist wound healing environment through the selection of the hydrogel-forming polymers. Alginate salts have varying degrees of water solubility such that one can manipulate the gelation of alginate by ion exchange interaction. As calcium ions rapidly coagulate alginate on contact and impede further penetration of additional calcium ions into the hydrogel alginate, the lower concentration of alginate in the hydrogel matrix results in a thicker film layer at the surface. To achieve the best film thickness in this embodiment, the sodium alginate can vary from 0.1% to 2% by weight and the calcium concentration can vary from 1% to 20% in the hydrogel.

In this embodiment of the wound care system, the basic hydrogel matrix is a mixture of sodium alginate, various polymers, glycerin, deionized water, various vitamins, and a preservative. The polymers produce the correct viscosity in the hydrogel. In this embodiment, carboxymethylcellulose (CMC) is used but other polymers can be substituted as long as viscosity is increased. Glyerin acts as a tackifier and prevents complete drying of the hydrogel in a wound lacking sufficient exudate. A major component of the hydrogel is sodium alginate, which dissolves in water, whereas calcium alginate does not. In addition, hydrogel-forming materials in the wound care system may include polyvinyl alcohol, modified cellulose, polyethylene glycol, dextrans, chitosan, acrylate polymers, acemannan as well as other similar substances. The primary hydrogel forming material is alginic acid.

The secondary hydrogel-forming polymer helps the wound care system achieve adequate viscosity. CMC is known to intermolecularly entangle with alginate polymers. The secondary hydrogel forming material may include polyvinyl alcohol, acrylate polymers, chitosan, acemannan, as well as other similar materials. In addition, the hydrogel matrix contains high molecular weight CMC to directly interact with alginate-containing hydrogels in the form of intermolecular hydrogen bonding. CMC is a modified form of plant cellulose with improved water solubility that is a major component of the hydrogel. The combination of alginate and CMC induce the ion exchange mediated film formation over the wound. The concentration of CMC can be varied to create a hydrogel matrix of appropriate thickness that will maintain integrity once applied to the skin. The concentration of CMC can range from 0.1% to 2% in this embodiment.

Tack agents serve to create a balance between adhesion and release in the present wound care system. A proper tack agent will not cling too aggressively to the wound, potentially causing pain when removed. Hydrogels typically require secondary dressings to maintain apposition to the skin and prevent the dislocation of the hydrogel covering from the skin. In the present embodiment, tack agents have been added to the hydrogel matrix to improve the tackiness or the stickiness of the material. Tack agents may include but are not limited to polyvinylpyrolidone, acrylates, rosin esters, as well as a variety of other similar materials.

Additionally, glycerol is also an effective tack agent since it is possesses the necessary tack, is highly water soluble, imparts a silky feeling to the hydrogel, and prevents or slows the hydrogel from prematurely drying in the absence of significant wound exudate. Glycerol not only serves as a tack agent in the wound care system but is also useful as a plasticizer, allowing for some flexibility of the film layer. Flexibility of the film layer is especially useful if the wound care system is to be applied over joints or in dynamic areas such as elbows, knees, or fingers. Glycerol may be present in the hydrogel matrix at ratios of 5% to 50% in this embodiment.

For therapeutic value, additional materials may be added to a finished hydrogel product such as vitamins such as A, D, or E. Cyclodextrans may also be added to the hydrogel to improve the solubility of any lipophilic vitamins that would otherwise be insoluble in an aqueous solution. Anesthetic agents such as amide or ester topical anesthetic agents; aloe vera, acemannan, or other plant-based healing agents may also be added to the hydrogel matrix to impart additional therapeutic benefits.

OBJECTS OF THE INVENTION

An object of the present invention is to provide a wound care system that absorbs exudates and keeps the wound moist to foster faster healing.

Another object of the present invention is to provide a transparent wound care system that does not obstruct the view of the fresh body art as it heals.

Another object of the present invention is to provide a wound care system that quickly adapts for use on wounds of various sizes and shapes.

Another object of the present invention is to provide a wound care system that promotes hemostasis by controlling and eventually stopping the flow of blood from damaged blood vessels.

Another object of the present invention is to provide a hydrogel wound covering that does not require a secondary dressing in order remain clear from debris or extraneous matter.

BRIEF DESCRIPTION OF THE DRAWINGS

Ref. 1 is the freshly applied tattoo;
Ref. 2 is the user's skin covered by tattoo;
Ref. 3 is undamaged skin adjacent to tattoo;
Ref. 6 is the film covering over tattoo and hydrogel.

DETAILED DESCRIPTION OF DRAWINGS

While the above description is of the preferred embodiment of the present invention, it should be appreciated that the invention may be modified, altered or varied without deviating from the scope and fair meaning of the following claims.

The present system and method for wound care dressing combines a hydrogel matrix and spray to create a transparent membrane or film layer. The spray interacts with the hydrogel to form a membrane over the skin which eliminates the need for a secondary dressing. The present wound care system plays a pivotal role in hemostasis, which involves constriction of the blood vessel, temporary blockage of the blood vessel and coagulation of blood until the damaged tissue is repaired. The hydrogel matrix blocks the damaged blood vessels and also keeps the coagulated blood and exudate contained and also traps moisture around the wound to promote faster healing in a moist wound healing environment. The flexible cover formed by the combination of the hydrogel matrix and the film layer also absorbs the exudate that seeps from the wound as the wound heals.

Figure 1:
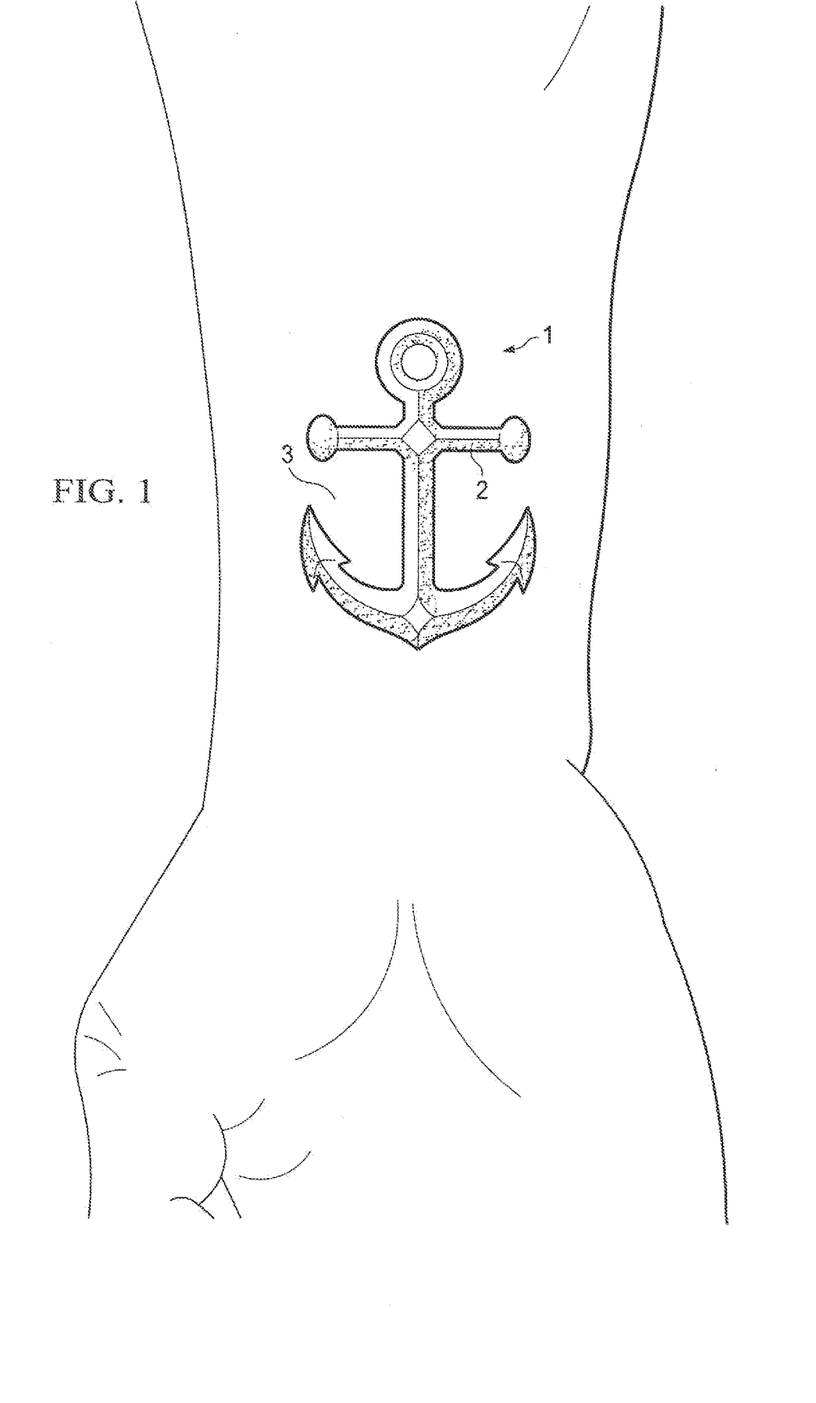
FIG. 1 is a view of a user with a fresh tattoo on the skin;
Ref. 1 is the freshly applied tattoo;
Ref. 2 is the user's skin covered by tattoo;
Ref. 3 is undamaged skin adjacent to tattoo.

FIG. 1 is a view of a user with a fresh tattoo on the skin. The tattoo is applied directly to the user's skin using needles and ink. As the tattoo is applied and the ink is deposited in the skin, ink and exudates are released from the skin. The skin immediately adjacent to the tattooed skin remains undamaged. After the completion of the tattoo, the wounded area is gently cleansed of any extraneous matter such as ink, blood, or surface exudates.

Figure 2:
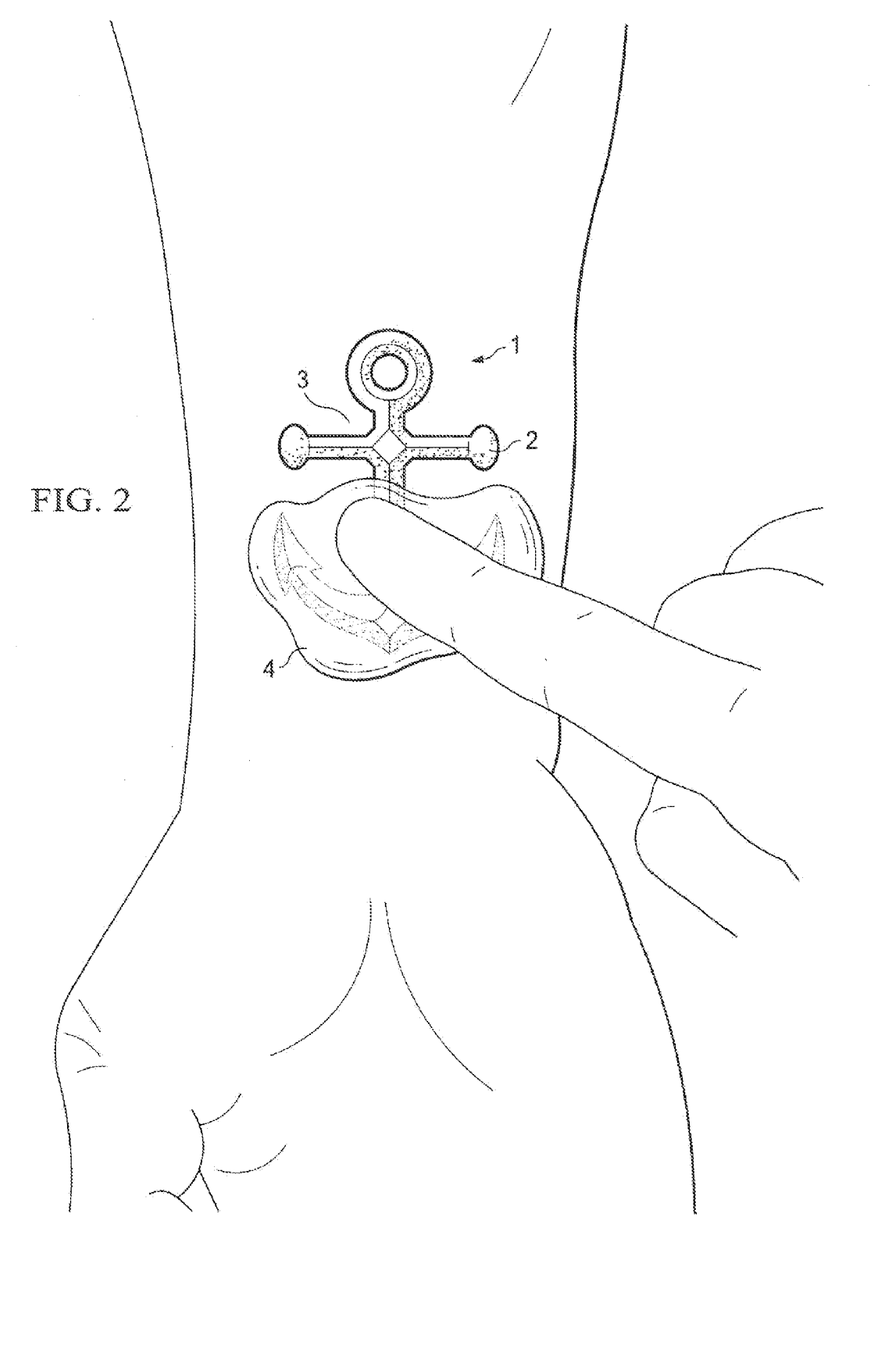
FIG. 2 is a view of the hydrogel being spread over the tattoo;
Ref. 1 is the freshly applied tattoo;
Ref. 2 is the user's skin covered by tattoo;
Ref. 3 is undamaged skin adjacent to tattoo;
Ref. 4 is hydrogel, spread over tattooed surface by user.

FIG. 2 is a view of the hydrogel matrix being spread over the tattooed surface. Once the application of the tattoo is complete and the tattooed skin surface has been cleared of any debris or extraneous matter, the hydrogel matrix is spread over the entire tattooed area of the skin as well as the adjacent, non-wounded skin immediately surrounding the freshly tattooed skin. The extension of the hydrogel matrix onto the undamaged skin helps secure the hydrogel matrix to the wounded area adjacent to the undamaged skin. The user would then treat the hydrogel matrix spread over the wound with a spray solution. As the spray covers the hydrogel matrix, a film cover is instantaneously created over the tattoo from the interaction of the hydrogel matrix and the spray. The wound care system is functional within seconds of combining the hydrogel matrix and the spray at the surface of the skin. In addition, the surface of the film cover is smooth and not tacky as a common hydrogel would be. Since the surface is not sticky after the wound care system sets, no additional wound dressing is required as is commonly required with traditional wound dressings and hydrogels. The wound is protected from airborne bacteria and other environmental elements. In addition, the wound is still visible to the tattoo owner and any additional observers who wish to see the tattoo. The interior surface of the wound care system adjacent to the skin absorbs exudate and maintains a moist wound healing environment, which decreases the formation of the exudative crust, while the exterior surface of the wound care system blocks foreign substances from coming into contact with the wound.

Figure 3:
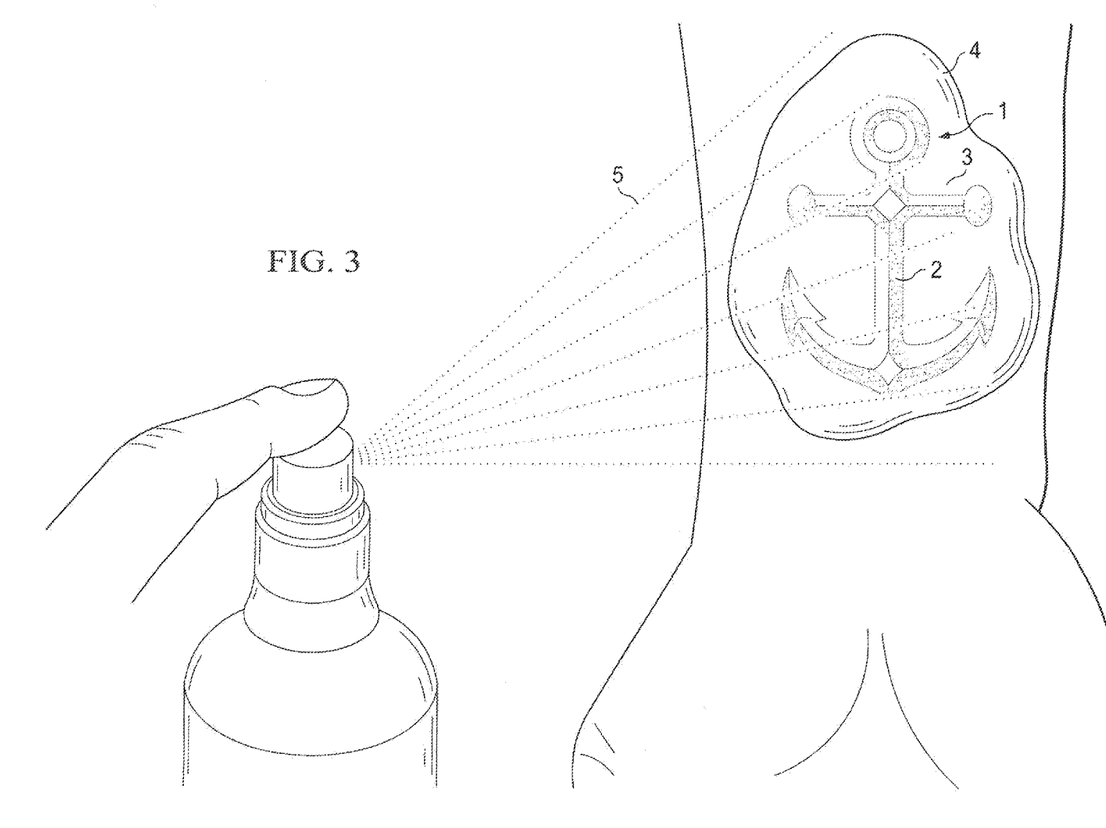
FIG. 3 is a view of the tattoo covered with spray;
Ref. 1 is the freshly applied tattoo;
Ref. 2 is the user's skin covered by tattoo;
Ref. 3 is undamaged skin adjacent to tattoo;
Ref. 4 is hydrogel spread over tattooed surface;
Ref. 5 is mist sprayed over hydrogel.

FIG. 3 is a view of the solution sprayed onto the surface of the hydrogel spread over the tattooed skin. As the spray covers the hydrogel matrix, a reaction occurs that creates a film cover over the wound. The wound care system is functional within seconds of combining the hydrogel matrix and the spray at the surface of the skin. In addition, after the film sets, the surface of the film is smooth and not tacky as one would expect a hydrogel coating to be. The hydrogel matrix is furthered strengthened by the presence of wound exudates as the additional moisture from the exudates keeps the hydrogel moist and strengthens the connection to the skin and tattooed surface. In addition, the wound care system decreases the formation of exudative crust, which is painful to remove and results in additional ink loss. As the exudates dries, the hydrogel matrix also dries and weakens.

Figure 4:
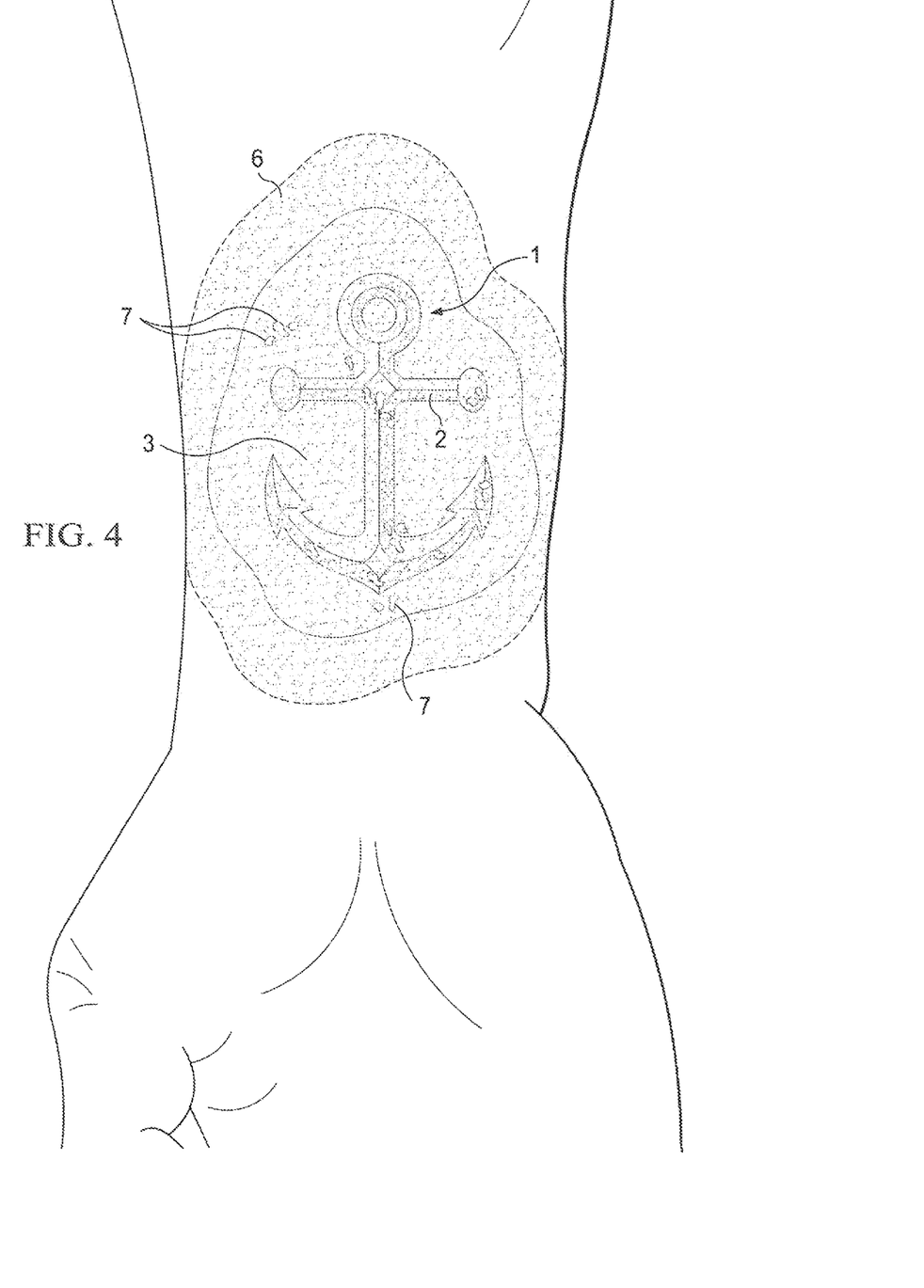
FIG. 4 is a view of the tattoo covered in film that has not set;
Ref. 1 is the freshly applied tattoo;
Ref. 2 is the user's skin covered by tattoo;
Ref. 3 is undamaged skin adjacent to tattoo;
Ref. 6 is the film covering over tattoo and hydrogel;
Ref. 7 is pooled exudate beneath hydrogel and film covering.

FIG. 4 is a view of the tattoo covered by the wound care system that has not yet set and is still moist on the exterior. Within a few seconds, the film will dry and become smooth and not tacky to touch. The film cover is transparent and flexible. The wound care system can be used on wounds or tattoos of various sizes, shapes, and diameters. The fresh tattoo can be seen by the users and passersby immediately after its application. In addition, the combined hydrogel and film cover foster a moist wound healing environment that encourages faster healing of the wound and lessens the formation of exudative crust which also decreases the loss of ink. Flexibility of the film layer is especially useful if the wound care system is to be applied over joints or in dynamic areas such as elbows, fingers, or knees. The hydrogel also gathers pooled exudate and blood and keeps them contained within the wound care system. As the exudates dries, the hydrogel matrix also dries and weakens. The drying hydrogel matrix begins to loosen from the surface of the skin. The wound care system is easily removed from the surface of the skin by gently rubbing the film surface with a moist towel until the wound care system detaches from the skin. Alternatively, the wound care system may be soaked in warm water, which will result in swelling as the hydrogel absorbs the water and will eventually release its bond to the skin.

Figure 5:
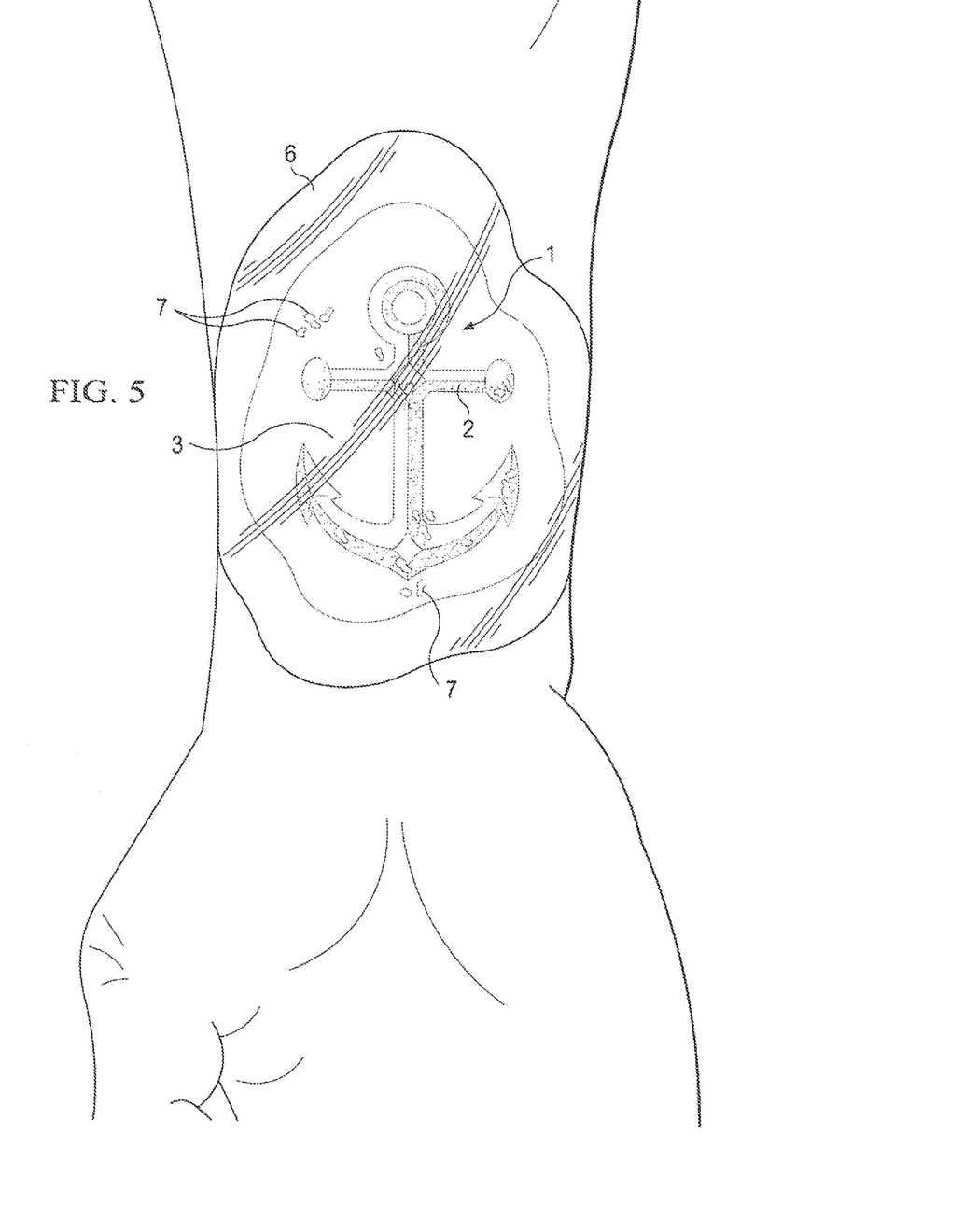
FIG. 5 is a view of the tattoo covered in film that has set;
Ref. 1 is the freshly applied tattoo;
Ref. 2 is the user's skin covered by tattoo;
Ref. 3 is undamaged skin adjacent to tattoo;
Ref. 6 is the film covering over tattoo and hydrogel;
Ref. 7 is pooled exudate beneath hydrogel and film covering.
Figure 6:
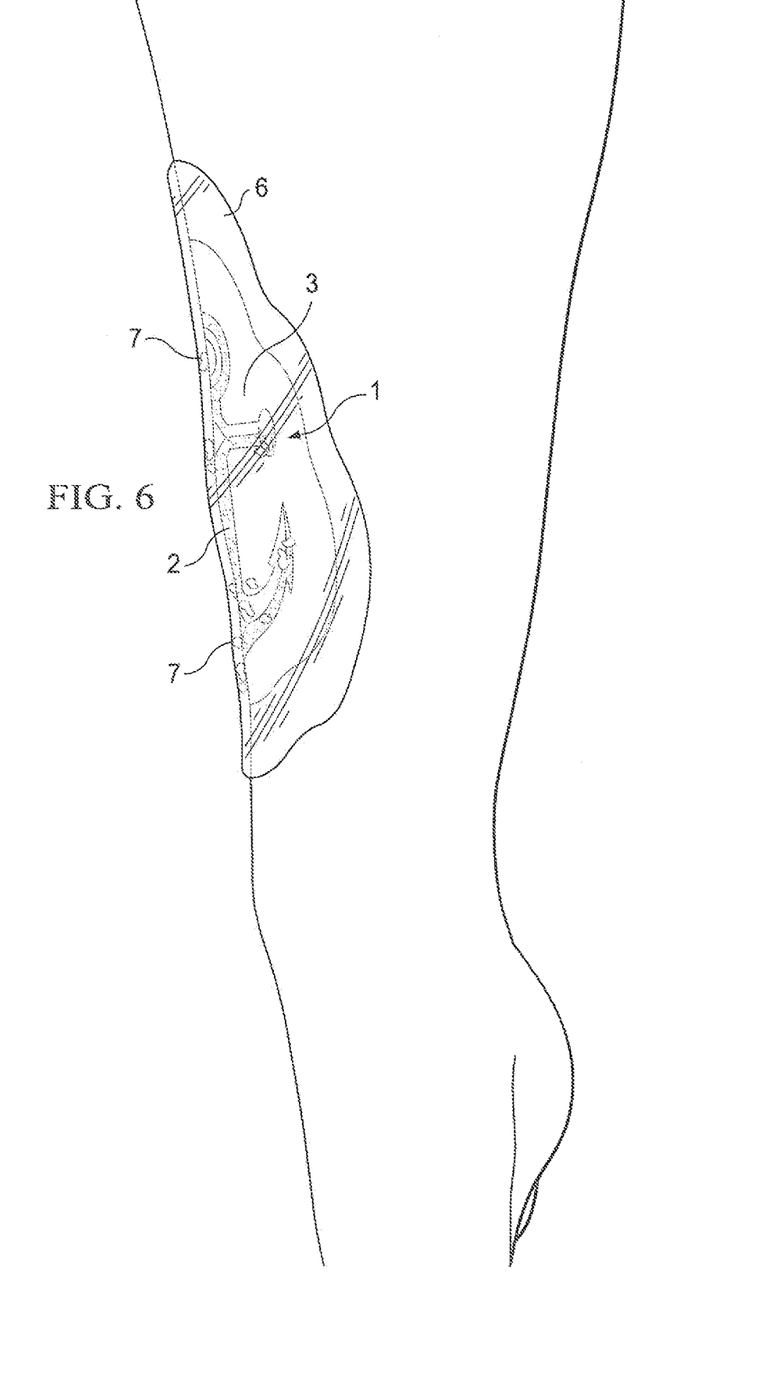
FIG. 6 is a side view of film covering the tattoo and undamaged skin;
Ref. 1 is the freshly applied tattoo;
Ref. 2 is the user's skin covered by tattoo;
Ref. 3 is undamaged skin adjacent to tattoo;
Ref. 6 is the film covering over tattoo and hydrogel;
Ref. 7 is pooled exudate beneath hydrogel and film covering.
Figure 7:
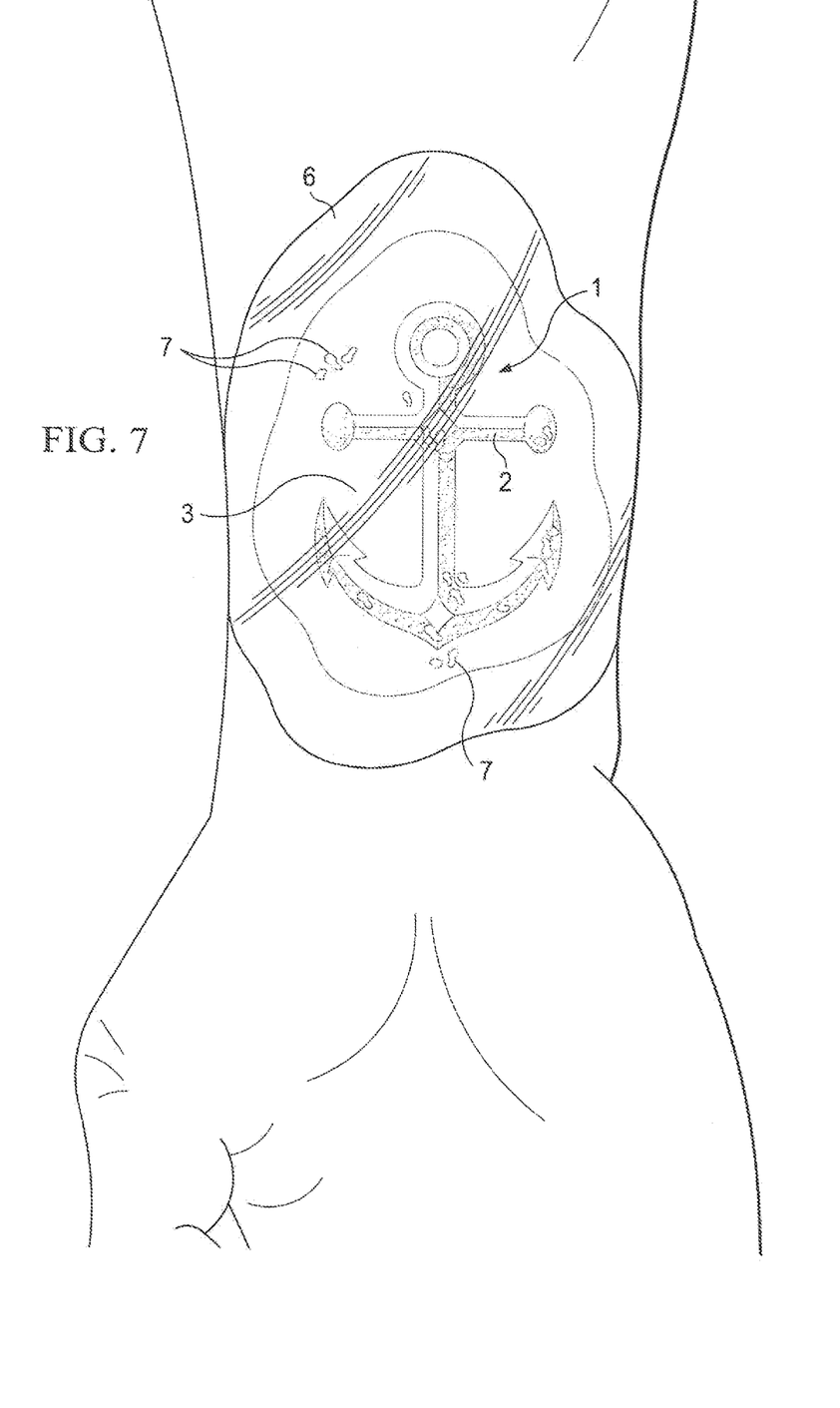
FIG. 7 is a front view of the tattoo covered in film;
Ref. 1 is the freshly applied tattoo;
Ref. 2 is the user's skin covered by tattoo;
Ref. 3 is undamaged skin adjacent to tattoo;
Ref. 6 is the film covering over tattoo and hydrogel;
Ref. 7 is pooled exudate beneath hydrogel and film covering.

FIG. 5 is the film layer after it has set and no longer moist at the exterior surface of the film layer. The interior surface of the applied wound care system is moist, absorbs exudate and prevents excessive ink loss from the freshly applied tattoo. FIG. 6 is the wound care system covering the freshly applied tattoo and extending to the undamaged, adjacent skin. The extension of the wound care system to the undamaged skin strengthens the bond of the wound care system to the skin and help control the pooled exudate within the wound care system. FIG. 7 shows the freshly applied tattoo on the user's skin covered by the film covering of the wound care system. The system extends onto the undamaged, adjacent skin and collects exudate that oozes from the fresh tattoo. The surface is not tacky and does not require a secondary dressing. The system is also flexible and will not be disturbed or dislodged by movement of the tattooed skin. In addition, the new tattoo owner can immediately see the colors and details of the tattoo art as well as allow others to view the fresh tattoo. Traditional dressings obscure the fresh tattoo as it heals. Impatient people may be tempted to remove the dressing to view the fresh tattoo and expose the wound to pathogens in the environment.

Figure 8:
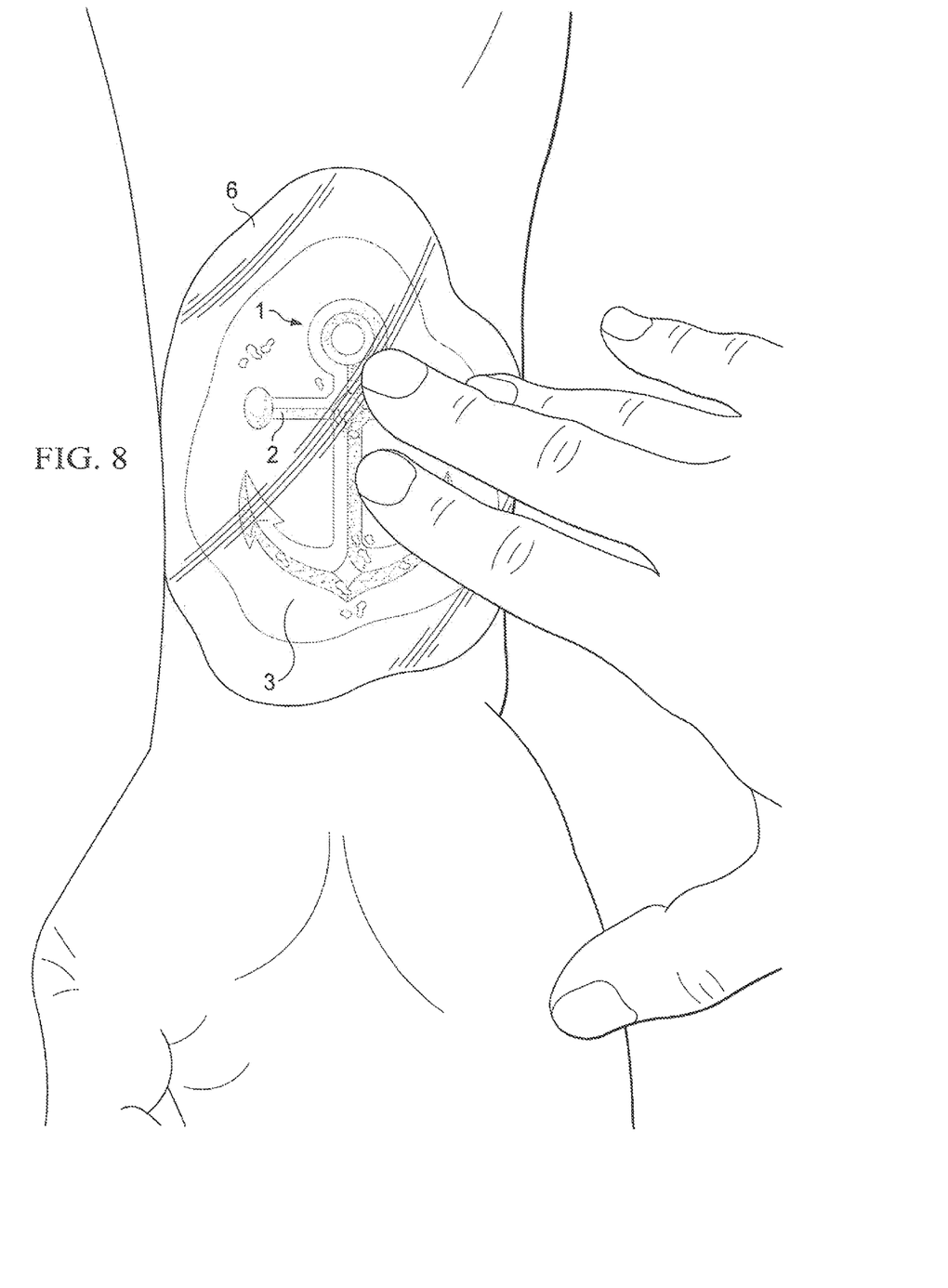
FIG. 8 is a front view of the non-tacky film covering;
Ref. 1 is the freshly applied tattoo;
Ref. 2 is the user's skin covered by tattoo;
Ref. 3 is undamaged skin adjacent to tattoo;
Ref. 6 is the film covering over tattoo and hydrogel.
Figure 9:
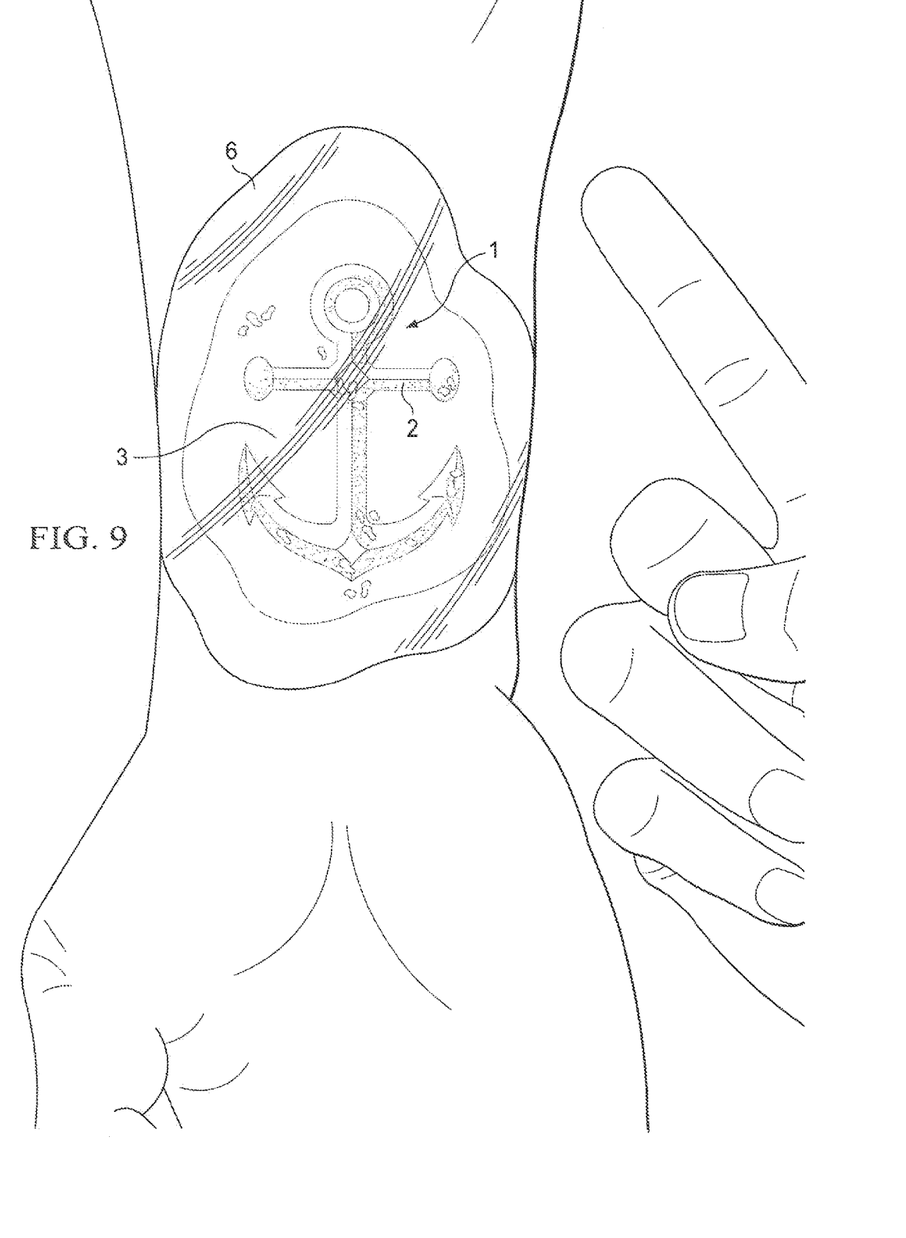
FIG. 9 is a front view of the dry film covering;
Ref. 1 is the freshly applied tattoo;
Ref. 2 is the user's skin covered by tattoo;
Ref. 3 is undamaged skin adjacent to tattoo;
Ref. 6 is the film covering over tattoo and hydrogel.
Figure 10:
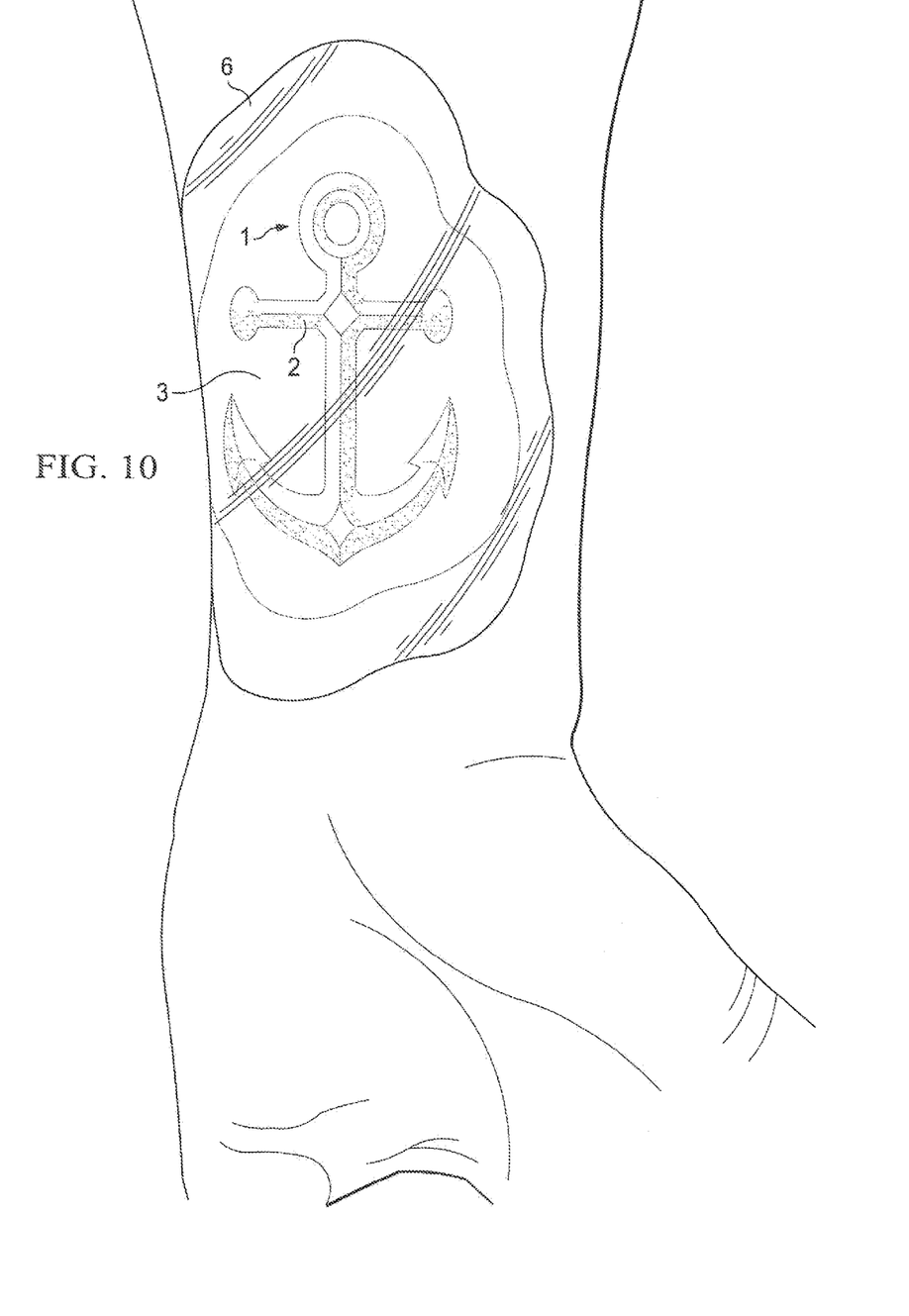
FIG. 10 is a front view of the film over tattooed skin in an extended, stretched position;
Ref. 1 is the freshly applied tattoo;
Ref. 2 is the user's skin covered by tattoo;
Ref. 3 is undamaged skin adjacent to tattoo;
Ref. 6 is the film covering over tattoo and hydrogel.
Figure 11:
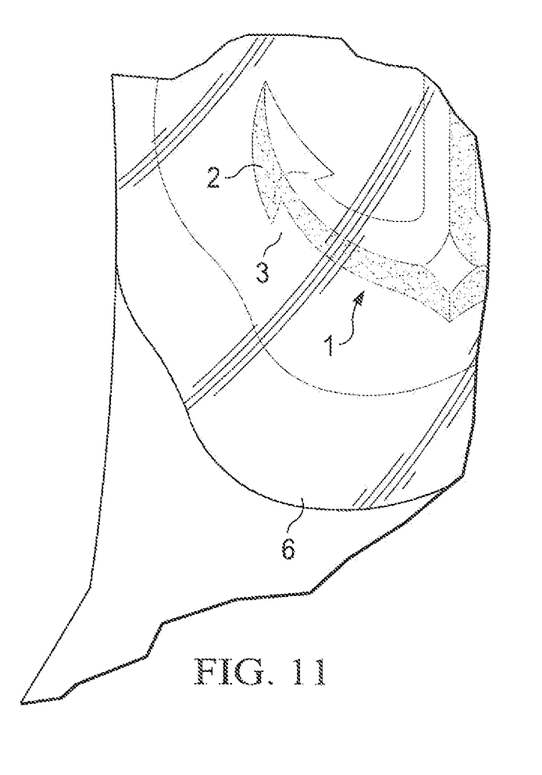
FIG. 11 is a close up view of the film cover over the tattoo;
Ref. 1 is the freshly applied tattoo;
Ref. 2 is the user's skin covered by tattoo;
Ref. 3 is undamaged skin adjacent to tattoo;
Ref. 6 is the film covering over tattoo and hydrogel.
Figure 12:
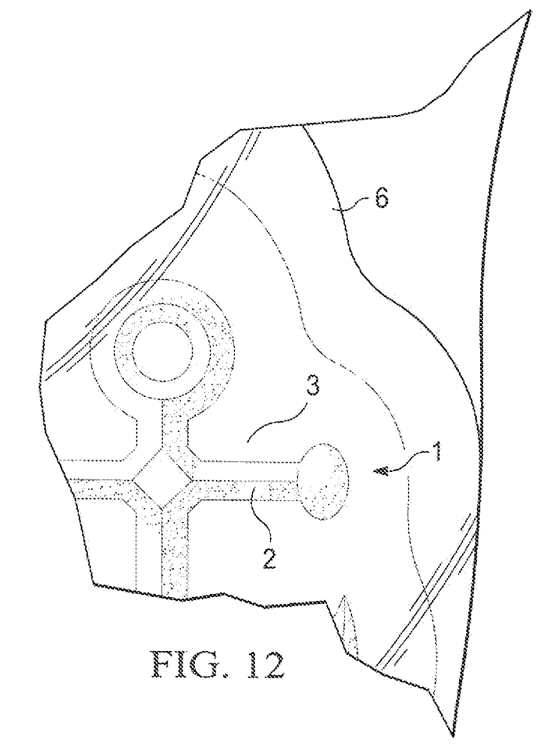
FIG. 12 is a close up view of the film cover over the tattoo.

FIG. 8 shows the surface of the film covering is not tacky or wet to the touch. The film covering is securely attached to the surface of the skin, covering both the fresh tattoo and the undamaged adjacent skin. FIG. 9 shows the surface of the film covering is dry and will not leave a residue on any surface that it comes into contact with. FIG. 10 shows the flexibility of the wound care system. The film covering is securely attached to the surface of the skin and will not dislodge or detach is the skin is stretched or extended as the user moves. This is particularly helpful for tattoos applied over joints or in dynamic areas such as elbows, knees, or fingers. FIGS. 11-12 are a close up views of the film covering over the tattooed skin. The film extends to the undamaged, adjacent skin to help secure the wound care system to the freshly tattooed skin, contain pooled exudate, and to maintain a moist wound environment.

What is claimed is:

1. A flexible and transparent membrane cover over a tattoo and aftercare system for tattoo consisting of:
   a non-crosslinked, transparent hydrogel polymer network spread consisting of sodium alginate and a liquid;
   a mineral spray solution containing a calcium compound;
   a tackifier;
   and the flexible, transparent membrane cover being formed by treating said non-crosslinked, transparent hydrogel polymer network spread on the tattoo with the mineral spray solution.

2. The flexible and transparent membrane cover over a tattoo and aftercare system for tattoo of claim 1, wherein the hydrogel polymer network spread reacts with the mineral spray solution to form the flexible, transparent membrane cover, wherein at least one ion from said mineral spray solution is transferred to the hydrogel polymer network spread.

3. The flexible and transparent membrane cover over a tattoo and aftercare system for tattoo of claim 1, wherein said liquid is selected from the group consisting of deionized water and alcohol.

4. The flexible and transparent membrane cover over a tattoo and aftercare system for tattoo of claim 1, wherein said tackifier is a glycerol solution.

5. The flexible and transparent membrane cover over a tattoo and aftercare system for tattoo of claim 1, wherein said mineral spray solution distributed over a layer of the hydrogel polymer network spread on a wounded skin surface creates the flexible and transparent membrane cover, wherein a proximate portion of the flexible and transparent membrane cover is adjacent to said wounded skin surface, wherein a distal portion of the flexible and transparent membrane cover is not adjacent to said wounded skin surface.

6. A flexible, transparent hydrogel membrane coating comprised of:
   a spreadable sodium alginate polymer network;
   a calcium solution;
   wherein said spreadable sodium alginate polymer network reacts with said calcium solution producing a flexible; transparent hydrogel membrane coating.

* * * * *